United States Patent [19]

Lee

[11] Patent Number: 5,141,008
[45] Date of Patent: Aug. 25, 1992

[54] DENTAL FLOSS APPLICATOR

[76] Inventor: Lawrence L. Lee, 3776 Martha St., San Diego, Calif. 92117

[21] Appl. No.: 700,752

[22] Filed: May 15, 1991

[51] Int. Cl.⁵ .............................................. A61C 15/00
[52] U.S. Cl. ................................... 132/325; 132/324
[58] Field of Search ............... 132/309, 323, 324, 325, 132/326, 327

[56] References Cited

U.S. PATENT DOCUMENTS

| D. 275,039 | 8/1984 | Loubier | D28/64 |
|---|---|---|---|
| 2,381,530 | 8/1945 | Dembenski | 132/325 |
| 3,592,203 | 7/1971 | Johnson | 132/323 |
| 3,861,406 | 1/1975 | Stitt | 132/325 |
| 4,214,598 | 7/1980 | Lee | 132/325 |
| 4,254,786 | 3/1981 | Won | 132/325 |
| 4,495,957 | 1/1985 | Beggs et al. | 132/325 |
| 4,512,354 | 4/1985 | Loubier et al. | 132/325 |
| 4,637,412 | 1/1987 | Martinez | 132/323 |
| 4,790,336 | 12/1988 | Kuo | 132/323 |
| 4,901,742 | 2/1990 | Olson | 132/325 |
| 4,966,176 | 10/1990 | Lachenberg | 132/325 |
| 5,020,554 | 6/1991 | Feinberg | 132/324 |
| 5,029,593 | 7/1991 | Huttunen | 132/325 |

FOREIGN PATENT DOCUMENTS 21411935  1/1985  United Kingdom ................ 132/325

Primary Examiner—Gene Mancene
Assistant Examiner—Frank A. LaViola

[57] ABSTRACT

A dental floss applicator having an elongated body, a bow across which the floss is to be stretched, a storage area for a supply of floss, a supply capstan for drawing the floss out of the storage area, a take-up capstan for disposal of the used floss, an axle to support the supply and take-up capstans, and guides to guide the floss between the bow and the capstans. The supply and take-up capstans are coaxial and integrated into one piece so that they rotate together as one rigid-body around the axle. The supply capstan is smaller in diameter than the take-up capstan, therefore, as the capstans are turned to advance the floss they also stretch the floss to generate floss tension. The axle is an extension of the body; it is hollow and it supports the capstans from a direction along the capstans common axis, on the side of the supply capstan (away from the take-up capstan). The guide is also an extension of the body, reaching axially over the supply capstan to guide the floss to the take-up capstan. The body is also hollow, thus providing rigidity while not having any thick areas that would be expensive to mold out of plastic.

12 Claims, 2 Drawing Sheets

DENTAL FLOSS APPLICATOR

BACKGROUND OF THE INVENTION

Dental floss applicators make dental floss easier to use. A dental floss applicator generally provides a frame for holding the floss and means for keeping the floss under tension, some even provide means for storage of floss and means for advancing the floss from the storage area to the positions where the floss perform the cleaning functions.

Among prior art dental floss applicators, the one described in U.S. Pat. No. 4,214,598 has been particularly effective. It has a double-capstan floss-advancing arrangement that enables easy advancing of floss into the cleaning position, the double-capstan mechanism furthermore positively stretches the floss as the floss is advanced. This stretching generates a high tension in the floss for easy insertion into the narrow space between the teeth to be cleaned. One embodiment of that invention has been manufacture by Flossrite Corp. of Fort Wayne, Ind. Effectiveness of that product has been recognized by the American Dental Association (ADA).

However, even the best among dental floss applicators must be improved from time to time. Already certain improvements on the original design has been disclosed in U.S. Pat. No. Des. 275,039 and U.S. Pat. No. 4,512,354.

Further improvements that has been sought after for a long time include: 1) Making the applicator more compact and more attractive in appearance, 2) making the applicator body more rigid, 3) reducing the thickness of the applicator body to reduce production cost, and 4) providing better uniformity of the floss tension.

Some of these improvements have unacceptable side-effects: For example, a very compact and attractive embodiment of the invention was already disclosed in the original patent (U.S. Pat. No. 4,214,598, FIG. 9); unfortunately, it turned out to be very difficult to wind floss onto that particular embodiment of the dental-floss applicator. The floss has to be threaded through a hole; and at some point, it has to be threaded under another part of the floss itself. The difficulty in winding makes this embodiment unacceptable.

In the dental floss applicator manufactured by Flossrite, the body had to be thick to provide the needed rigidity. The body could have been made both thin and rigid if it could have been made hollow, but the specific shape does not allow the part to be easily molded of plastic and be hollow on the inside. And if the body were made hollow (deeply concave) on the outside, then it would be difficult to clean. So the applicator body had to be made thick. The thickness of the applicator body is alos mainly responsible for the sometimes poor uniformity of the floss tension.

It is therefore highly desirable to have a dental floss applicator that combines all the attractive features of the embodiments disclosed in U.S. Pat. No. 4,214,598 without the specific problems. The present invention provide such a dental floss applicator. It is as compact as the embodiment shown in FIG. 9 of the patent, it is even more attractive in appearance, yet it is not at all difficult to wind floss on. The present invention furthermore allows the applicator body to be easily molded out of plastic, hollow on the inside, easy to clean, thin-walled, and rigid.

SUMMARY OF THE INVENTION

The present invention provides an improvement over prior art dental floss applicators described in U.S. Pat. No. 4,214,598. The present invention retains the features of having a double-capstan floss-advancing arrangement that enables easy advancing of floss into the cleaning position and furthermore stretches the floss to generate more tension as the floss is advanced.

One embodiment of the present invention comprises a dental floss applicator having an elongated body, a bow across which the floss is to be stretched, a storage area for a supply of floss, a supply capstan for drawing the floss out of the storage area, a takeup capstan for disposal of the used floss, an axle to support the supply and takeup capstans, and guides to guide the floss between the bow and the capstan.

The supply capstan and the takeup capstan are coaxial and integrated into one piece so that they rotate together as one rigid-body around the axle.

The supply capstan is smaller in diameter than the takeup capstan such that as the capstans are rotated to advance the floss, more floss is deposited onto the takeup capstan than drawn forward by the supply capstan, thus stretching the floss between the two capstans and generating a high tension in the floss to facilitate insertion of the floss into the area between the teeth to be cleaned.

The axle is an extension of the body; it is hollow and oriented along the longitudinal axis of the body; it supports the capstans from a direction along the capstans' common axis, on the side of the supply capstan away from the takeup capstan.

The guide is also an extension of the body, it reaches axially over the supply capstan to guide the floss to the takeup capstan.

The body is also hollow, it has a hole that extends more than one-third of the distance from the position of the capstans to the bow, thus enabling the body to be rigid while not having any thick areas that would be expensive to mold out of plastic.

Optionally, the dental floss applicator also has ratchet teeth along some of the contact area between the capstans and the axle to prevent rotation of the capstans in the reverse direction. It may also be equipped with a floss cutter and clip attached to the takeup capstan.

The present invention provides a dental floss applicator that, when compared to the prior art, is more compact, more attractive in appearance, easy to wind floss on, provides more uniform tension on the floss, requires the use of fewer parts, and the parts are easy to mold out of plastic, hollow on the inside, easy to clean, thin-walled, and more rigid.

DETAILED DESCRIPTION OF THE PREFERRED EMBODIMENTS

Figure 1:
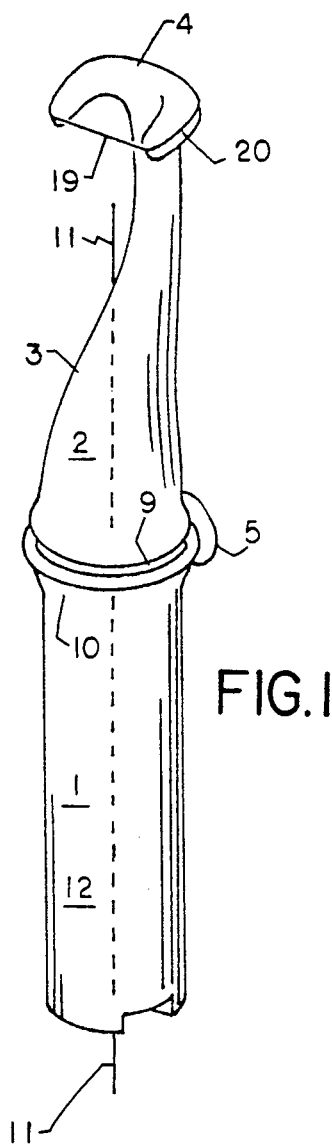
FIG. 1 is a perspective view of a preferred embodiment of this invention.
Figure 2:
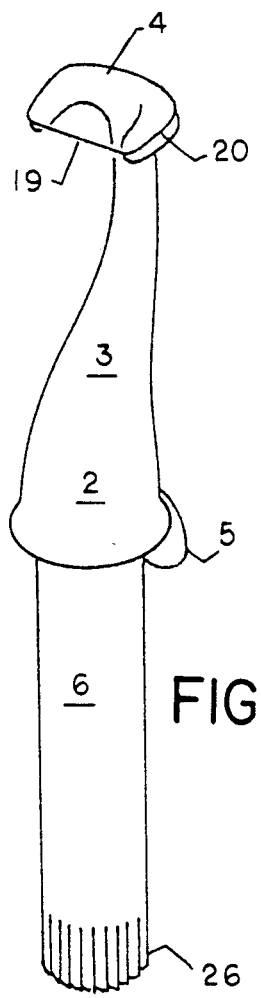
FIG. 2 is a perspective view of the preferred embodiment of FIG. 1 without the capstans and handle.

One preferred embodiment of the invention is shown in FIGS. 1-5. The dental floss applicator 1 comprises an elongated body 2 that extends out to a neck 3; at one end of the neck 3 is a bow 4, and at the other end of the neck 3 are a button 5 and a cylinder 6. The cylinder 6 is hollow. Its hollow interior serves as a storage area 7 for a supply of floss 8.

Positioned around the cylinder 6 are the supply capstan 9, and the takeup capstan 10. The supply and takeup capstans 9 and 10 are coaxial and they are integrated into one hollow piece of plastic that is free to rotate together as a single rigid-body around the cylinder 6, using cylinder 6 as an axle. The longitudinal axis 11 of cylinder 6 is then also the capstans' axis of rotation. The takeup capstan 10 tapers into a cylindrical shape where it also serves as a handle 12.

In a reference frame fixed to the body 2 of the dental floss applicator 1, the capstans 9 and 10 are supported by the cylinder 6 (the support means), cylinder 6 is an extension of the body 2 and it supports the capstans 9 and 10 from a direction along the capstans' common axis 11 on the side of the supply capstan 9 away from the takeup capstan 10. In operation, the supply of floss 8 is placed into the storage space 7 inside the cylinder 6 inside the handle 12. A strand 13 of the floss is threaded through a longitudinal slot 14 (FIG. 3) which runs through the entire length of the cylinder 6. The floss 13 comes out through the space 15 between the neck 3 and the supply capstan 9 (see FIGS. 3 and 4).

Figure 3:
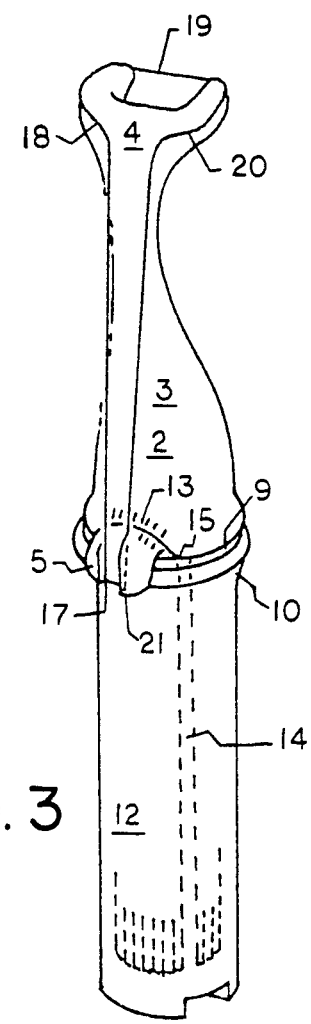
FIG. 3 is another perspective view of the preferred embodiment of FIG. 1 from a different angle.
Figure 4:
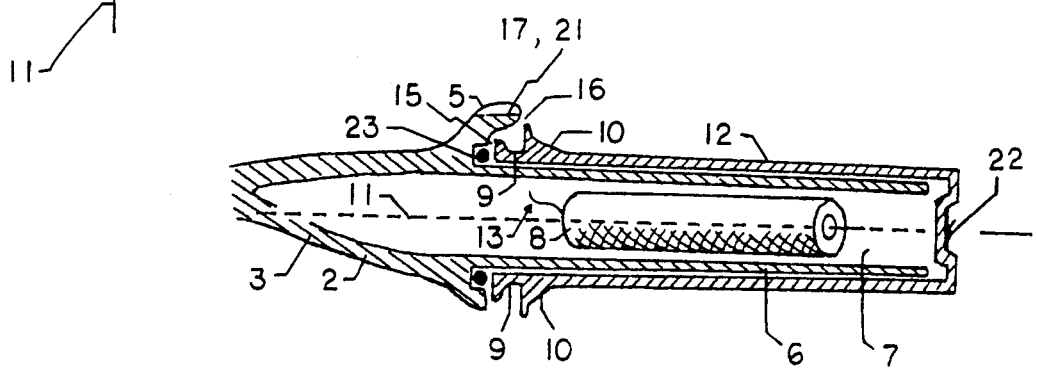
FIG. 4 is a longitudinal sectional view of part of the preferred embodiment of FIG. 1.
Figure 5:
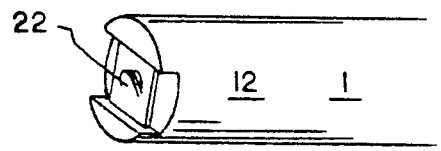
FIG. 5 is a perspective view of the bottom of the preferred embodiment of FIG. 1.

The floss 13 is first wound once around the button 5, in a generally counterclockwise (CCW) direction as seen in FIG. 3. Then the floss 13 is wound several times (preferably 2-4 times) around the supply capstan 9, also in a generally CCW direction as seen in FIGS. 1 and 3. As the floss is wound around the supply capstan 9, it must be tucked under the button 5. The tucking in is not difficult, a strand of floss extending tangentially out of the supply capstan 9 (or up to 20 degrees to the right of the tangent as seen in FIG. 4) during the winding process will tuck itself in as it is wound onto the capstan 9. Ample space at position 16 (see FIG. 4) has been provided for tucking in the floss.

After being wound around the supply capstan 9, the floss is threaded into a groove (guide means) 17 on button 5 to be guided towards the bow 4 where it is guided by groove (guide means) 18 to the position 19 for cleaning teeth. Then the floss is guided by groove (guide means) 20 on its way back to the button 5.

The floss returning from the bow 4 to the button 5 is threaded into a groove (guide means) 21 to be guided towards the takeup capstan 10. The grooves 17 and 21 in this embodiment happens to be one and the same; one side of it (the left side as seen in FIG. 3) functions as the guide 17 from the supply capstan 9 and the other side (the right as seen in FIG. 3) serves as the guide 21 to the takeup capstan 10.

The grooves (guide means) 17 and 21, and the button 5 are extension of the body 2. The button 5 is shown in FIG. 4 reaching axially (in a direction along the common axis 11 of the capstans) over the supply capstan 9 to guide the returning floss to the takeup capstan 10.

The floss is wound several times around the takeup capstan 10 in the same direction as it was wound around the supply capstan 9 (CCW as seen in FIGS. 1 and 3). The loose end of the floss may be held onto the handle 11 by means of an O-ring or a rubber band (not shown in the figures). Optionally, a metal clip-and-cutter 22 (FIGS. 4 and 5) is provided for cutting off excess floss and for holding the loose end.

When the handle 12 is turned in a generally CCW direction as seen in FIGS. 1 and 3, it is turned in the forward direction; floss is drawn from the supply of floss 8 in the storage area 7, out through space 15, CCW around the button 5, CCW around supply capstan 9, through guide grooves 17 and 18 to the position 19 where it is used for cleaning teeth; the used floss is guided by grooves 20 and 21 to the takeup capstan 10. In its motion around the applicator, the floss slides around the button 5, and through the guide grooves 17, 18, 20 and 21; it also slides through the cleaning position 19; but it is held fast by friction onto the supply and takeup capstans 9 and 10, sliding only very little; and it slides only axially as arrival of new floss displaces the existing floss sideways.

The takeup capstan 10 is conical in shape at the position where the used floss first lands onto the capstan, Tension of the floss and arrival of more floss gradually push the floss down the conical section to the cylindrical section. The effective diameter of the takeup capstan 10 is its diameter d1 at the position where the floss first touches the capstan (the effective diameter d1 will also sometimes be referred to as just "diameter"). For every complete revolution of the capstan 10, a length of floss $\pi$ d1 is wound onto the takeup capstan 10. The torque exerted by the floss on the takeup capstan 10 is (f1 $\times$ d1)/2 where f1 is a force due to the tension of the floss at the takeup capstan 10.

The supply capstan 9 is substantially cylindrical, it has a diameter d2. For every complete revolution of the supply capstan 9, a length of floss $\pi$ d2 is drawn from the supply 8. The torque exerted by the floss on the supply capstan 9 is (f2 $\times$ d2)/2 where f2 is a force due to the tension of the floss at the supply capstan 9.

The diameter d2 of the supply capstan 9 is smaller than the (effective) diameter d1 of the takeup capstan 10 (typically d1 is 22.5 mm and d2 is 21.5 mm); so as the capstans 9 and 10 are turned in the forward direction to advance floss, more floss is taken up by the takeup capstan 10 than supplied by the supply capstan 9. For every complete revolution of the capstans, the difference is $\pi$ (d1 $-$ d2). Thus the floss in it path between these two capstans is stretched by this amount. It is this stretching that generates the exceptionally high tension in dental floss applicators with this type of double-capstan mechanism.

The double-capstan mechanism that advances the floss while stretching the floss to generate tension was described in U.S. Pat. No. 4,214,598. All embodiments of that prior art invention (including the present invention) have this feature.

For the double-capstan mechanism to function properly, there must be some friction between the floss and the capstans. The friction is usually self-regenerating: any small amount of tension on the floss generates friction, and friction generates more tension. But it works only if there is some small friction to begin with. As a reliable source of this initial friction, an optional rubber O-ring 23 is provided at the position 15 to pinch on the floss as it exits from the storage area 7.

The tension of the floss generates a torque to turn the capstans in the reverse direction. Typically this torque is counteracted by friction between the capstans and its support members. The net torque in the reverse direction is the difference between the torque on the takeup capstan 10, (f1×d1)/2, and that on the supply capstan 9, (f2×d2)/2. It has already be mentioned that d1 is always larger than d2. Generally, f1 is also larger than f2 because of the frictions between the floss and the guides 17, 18, 20 and 21. Fortunately, the net reverse torque is usually quite small. The restraining friction should also be made as small as possible because any friction that is applied to counteract reverse motion of the capstans will also impede forward rotation.

In the embodiment shown in FIGS. 1-7 of the present invention, the capstans 9 and 10 are supported by the cylinder 6 which functions as an axle. Cylinder 6 supports the capstans from a direction along the capstans' common axis 11 on the side of the supply capstan 9 away from the takeup capstan 10. In contrast, the prior art embodiments described in U.S. Pat. No. 4,214,598 all have supply and takeup capstans integrated into one piece with an axle between the capstans, and the axle is supported by a bearing which supports the capstans from a direction perpendicular to the capstans' common axis.

In the embodiment of the prior art invention manufactured by Flossrite Corp, the friction between the capstans and its support members had been difficult to control because both parts (the capstan axle and its support bearing) are made of thick section of rigid plastic, so a small variations in the dimensions of the molded parts causes large variations of the friction.

In the present invention, the friction between the capstans 9 and 10 and the axle 6 can be controlled much more easily because the axle 6 is hollow, thin-walled and slotted, so it functions well as a relatively weak spring to apply a uniform force to the internal surface of the handle 12.

Figure 6:
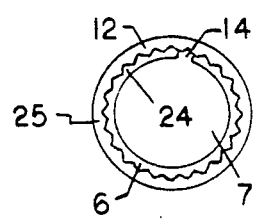
FIG. 6 is a bottom view of another preferred embodiment of this invention.
Figure 7:
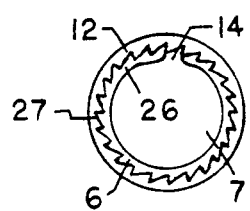
FIG. 7 is a bottom view of the preferred embodiment of FIG. 1.

Instead of using friction (or in addition to using friction) for preventing reverse rotation of the capstans, the capstans 9 and 10 can be held against reverse rotation by the use of teeth 24-27 as shown in FIGS. 3, 6, and 7. The teeth 24 and 25 may be symmetrical as shown in FIG. 6 in which case forward and reverse rotation of the capstans are impeded equally. Alternatively, the teeth 26 and 27 may be a ratchet type as shown in FIG. 7 in which case the reverse rotation is impeded to a much higher degree than forward rotation. In either case, the internal and external teeth need not have the same pitch (spacing between teeth); therefore the numbers of internal and external teeth may also be different. If the pitch is different, and the teeth are uniformly spaced, then the teeth will only be engaged at a smaller number of positions (this number is the highest common factor of the numbers of teeth) but the teeth will be engaged at many more angular positions (this number of angular positions is the least common multiple of the numbers of teeth). For example, if there were 50 internal teeth and 60 external teeth, then only ten teeth at a time are engaged, but there are 300 angular positions where some teeth are engaged. It is sometimes advantageous to have unequal number.

The most obvious difference between the dental floss applicator shown in FIGS. 1-5 of the present invention and the model manufactured by Flossrite is the way the capstans are mounted: Flossrite's model has transversely mounted capstans (transverse to the direction of elongation for the applicator's body) whereas the embodiments shown here in FIGS. 1-5 have longitudinally mounted capstans. The transverse mounted capstans needs to be turned with a knob, so there is a knob sticking out. The longitudinally mounted capstans are turned by turning the whole handle, so there is no need for a knob. The applicator looks neater without the knob.

In U.S. Pat. No. 4,214,598, one embodiment of the invention was illustrated (FIG. 9) that has longitudinally mounted capstans. However, it turned out to be very difficult to wind floss onto that particular embodiment of the dental floss applicator. Because of the winding problem, that embodiment was never put into production. The problem of difficult winding was solved in the present invention by changing the direction of supporting the capstans and the use of guide means (principally guide 21) that reaches over the supply capstan 9 to guide the floss to the takeup capstan 10.

Not having a knob in the way also enables the applicator body of the present invention to have a hollow section extending most of the way towards the bow 4. Rigidity is most critically needed in the section of the body nearest the handle, especially the first one-third to one-quarter of the distance from the capstans to the bow; and in the present invention, that section has been made hollow to provide rigidity without using thick sections of material.

Figure 8:
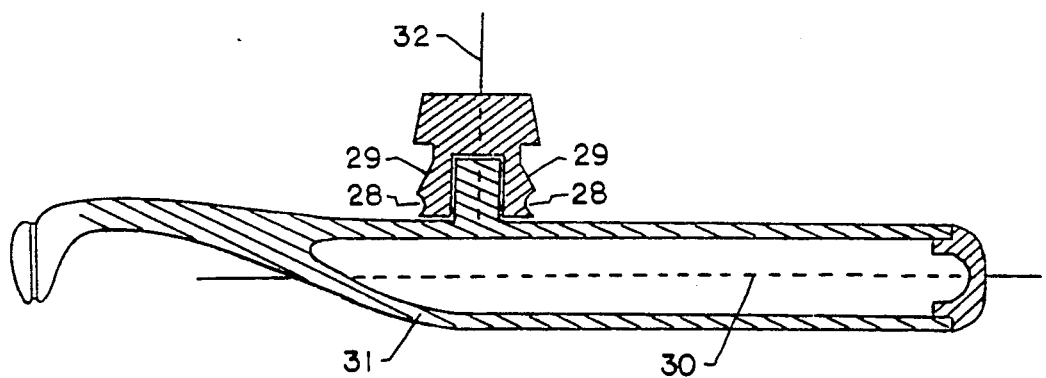
FIG. 8 is a longitudinal sectional view of another preferred embodiment of this invention.

The capstans do not have to be longitudinally mounted to allow the body to be made hollow: an example is shown in FIG. 8, where the supply and takeup capstans 28 and 29 are transversely mounted (transverse with respect to the longitudinal direction 30 of the body 31) yet the body 31 is hollow. The capstans are however supported from a direction along the capstans' common axis 32, on the side of the supply capstan 28 away from the takeup capstan 29 as in the other embodiments of the present invention, and in this respect differ from all the embodiments described in U.S. Pat. No. 4,214,598.

Compared to the prior art dental floss applicators, the present invention has the following improvements: 1) It requires the use of fewer parts, 2) the device can be made more compact, 3) the most critical parts of the body can be made hollow, thus enabling the apparatus to be made more rigid, and 4) friction on the capstans can be made more uniform.

While there have been described above the principles of this invention in connection with specific apparatus, it is to be clearly understood that this description is made only by way of example and not as a limitation to the scope of the invention.

I claim:

1. A dental floss applicator for use in dispensing and supporting a strand of dental floss under tension for cleaning teeth comprising an elongated body, a bow across which the floss is to be stretched, a storage area for a supply of floss, a supply capstan for drawing the floss out of the storage area, a take-up capstan for disposal of the used floss, support means for supporting the supply and take-up capstans at a predetermined position relative to the body while allowing the capstans to rotated with respect to the body, and guide means to guide the floss between the bow and the capstans;

said supply capstan and said take-up capstan being coaxial and integrated into one piece so that they rotate together as one rigid body; said supply capstan having two sides, one said side being directed towards said take-up capstan and the other side away from the take-up capstan;

said supply capstan being smaller in diameter than said take-up capstan such that as the capstans are rotated to advance the floss, more floss is deposited onto the take-up capstan than drawn forward by the supply capstan, thus stretching the floss between the two capstans and generating a high tension in the floss to facilitate insertion of the floss into the area between the teeth to be cleaned;

said support means being fixed and supporting the capstans and allowing said capstans to rotate with respect to said support means, said support means supporting the capstans from the side of the supply capstan away from the take-up capstan;

said guide means reaching axially over the supply capstan to guide the floss to the take-up capstan.

2. A dental floss applicator according to claim 1 wherein said supply and take-up capstans are supported to enable rotation around an axis that is generally parallel to the direction of elongation of the body.

3. A dental floss applicator according to claim 2 wherein said support means is an axle through the supply and take-up capstans.

4. A dental floss applicator according to claim 3 wherein said axle is hollow; said body being also hollow; the hollow part of said body extending through said hollow portion of said axle thus providing a storage area for the floss, and enabling the hollow body to be structurally rigid while not having any thick areas that would be expensive to mold out of plastic.

5. A dental floss applicator according to claim 4 further having teeth along some of the contact area between said capstans and said axle to impede rotation of the capstans around the axle.

6. A dental floss applicator according to claim 5 wherein said teeth are ratchet teeth such that rotation of the capstans in the direction to advance floss is impeded by a lesser degree than rotation in the opposite direction.

7. A dental floss applicator according to claim 6 further having a floss cutter attached to the take-up capstan.

8. A dental floss applicator according to claim 6 wherein said teeth include teeth attached to the capstans and teeth attached to the body, the teeth attached to the capstans are different in pitch from the teeth attached to the body, thus providing a larger number of positions where some teeth are engaged than the total number of teeth.

9. A dental floss applicator according to claim 1 wherein said support means is an axle through the supply and take-up capstans.

10. A dental floss applicator according to claim 1 wherein said body is hollow; thus providing a storage area for the floss, and is furthermore structurally rigid while not having any thick areas that would be expensive to mold out of plastic.

11. A dental floss applicator for use in dispensing and supporting a strand of dental floss under tension for cleaning teeth comprising an elongated body, a bow across which the floss is to be stretched, a storage area for a supply of floss, a supply capstan for drawing the floss out of the storage area, a take-up capstan for disposal of the used floss, support means for supporting the supply and take-up capstans at a predetermined position relative to the body while allowing the capstans to rotated with respect to the body, and guide means to guide the floss between the bow and the capstan;

said supply capstan and said take-up capstan being coaxial and integrated into one piece so that they rotate together as a single rigid body; said supply capstan having two sides, one said side being directed towards said take-up capstan and the other side away from the take-up capstan;

said supply capstan being smaller in diameter than said take-up capstan such that as the capstans are rotated to advance the floss, more floss is deposited onto the take-up capstan than drawn forward by the supply capstan, thus stretching the floss between the two capstans and generating a high tension in the floss to facilitate insertion of the floss into the area between the teeth to be cleaned;

said support means being fixed and supporting the capstans and allowing said capstans to rotate with respect to said support means, said support means supporting the capstans from the side of the supply capstan away from the take-up capstan;

said body being hollow over at least half of its length, and having a hollow portion which extends over at least one quarter of the distance from the position of the capstans to the position of the bow.

12. A dental floss applicator according to claim 11 wherein said hollow portion of the body extends over at least one third of the distance from the position of the capstans to the position of the bow.

* * * * *